(12) United States Patent
Young et al.

(10) Patent No.: US 11,497,825 B2
(45) Date of Patent: *Nov. 15, 2022

(54) ERGONOMIC SCENT DIFFUSER

(71) Applicant: Aeron Lifestyle Technology, Inc., Fairfield, IA (US)

(72) Inventors: Christopher E. Young, Rushville, IL (US); Patrick Guerin, Fairfield, IA (US)

(73) Assignee: Aeron Lifestyle Technology Inc., Fairfield, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/359,755

(22) Filed: Jun. 28, 2021

(65) Prior Publication Data
US 2021/0322617 A1    Oct. 21, 2021

Related U.S. Application Data

(63) Continuation of application No. 16/287,109, filed on Feb. 27, 2019, now Pat. No. 11,083,812.

(51) Int. Cl.
*A61L 9/03*    (2006.01)
*B60H 3/00*    (2006.01)
*B01F 23/21*    (2022.01)

(52) U.S. Cl.
CPC .............. *A61L 9/03* (2013.01); *B60H 3/0014* (2013.01); *A61L 2209/131* (2013.01); *A61L 2209/133* (2013.01); *A61L 2209/15* (2013.01); *B01F 23/215* (2022.01)

(58) Field of Classification Search
CPC ... A61L 9/00; A61L 9/015; A61L 9/02; A61L 9/03; B01F 23/00; B01F 23/20; B01F 23/21; B01F 23/215; B60H 3/00; B60H 3/0007; B60H 3/0014
See application file for complete search history.

(56) References Cited

U.S. PATENT DOCUMENTS

| | | | | |
|---|---|---|---|---|
| 4,968,456 A | * | 11/1990 | Muderlak | A61L 9/122 137/60 |
| 6,241,161 B1 | * | 6/2001 | Corbett | A01M 31/008 222/187 |
| 8,983,277 B2 | * | 3/2015 | Hsiao | A61L 9/16 392/386 |
| 11,083,812 B2 | * | 8/2021 | Young | B60H 3/0014 |
| 2016/0256585 A1 | * | 9/2016 | Esses | H05B 3/03 |

* cited by examiner

*Primary Examiner* — Natasha E Young
(74) *Attorney, Agent, or Firm* — Zarley Law Firm P.L.C.

(57) ABSTRACT

An ergonomic scent diffuser having a first housing with electrical components connected to a second housing having a heating element disposed within. Slidably connected to the second housing is a cap. The cap has depressions adjacent an outer end to provide an ergonomic grip. The cap also has guide rails and retaining members that retain and position a fragrance emitting member over the heating element.

14 Claims, 3 Drawing Sheets

ERGONOMIC SCENT DIFFUSER

CROSS REFERENCE TO RELATED APPLICATION

This application claims the benefit of priority and is a continuation of application Ser. No. 16/287,109, now U.S. Pat. No. 11,083,812, filed Feb. 27, 2019, the contents of this application is hereby incorporated by reference in its entirety.

BACKGROUND OF THE INVENTION

The present invention is directed to a scent diffuser and more particularly a scent diffuser having an ergonomic cap and capable of holding more fragrance.

Scent diffusers are known in the art and typically involve a fragrance pad that has absorbed a fragrant liquid being exposed to a heat element. Exposure to the heat causes the liquid to evaporate and disperse a scented gas. While useful, replacing and or reloading pads is difficult because it's hard to remove the pads and it's also easy to insert the diffuser in a power source upside down where the pad is below the heating source. Also, current diffusers are limited in the amount of fragrance that can be used. Accordingly, a device that addresses these deficiencies is needed in the art.

An objective of the present invention is to provide a scent diffuser that is more ergonomical to use.

Another objective of the present invention is to provide a scent diffuser that holds more fragrance.

These and other objectives will be apparent to those skilled in the art based upon the following written description, drawings and claims.

SUMMARY OF THE INVENTION

An ergonomic scent diffuser includes a first housing connected to a second housing and a cap removeably connected to the second housing. The first housing has electrical components adapted to transmit power from a power source to a heating element disposed within the second housing.

The cap has depressions on the top and the bottom adjacent an outer end to provide an ergonomic grip. Extending from the outer end of the cap through a chamber and beyond an inner end of the cap are a pair of guide rails and a pair of retention members. The guide rails are positioned to align with and be slidably received within guide grooves of the second housing. The retaining member is positioned to receive and retain the fragrance emitting member. Preferably, the fragrance emitting member is a resilient solid block molded into a protective tray. The tray prevents user error resulting in melted fragrance fusing components of the unit together. The tray also prevents the block from losing shape when heated and then cooled.

DETAILED DESCRIPTION OF THE PREFERRED EMBODIMENTS

Figure 1:
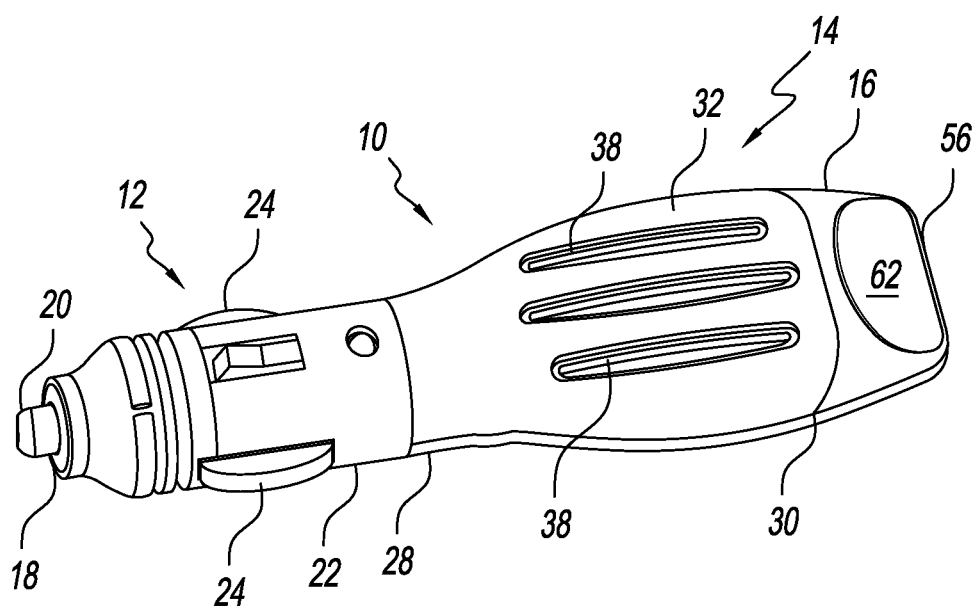
FIG. 1 is a perspective view of a scent diffuser.
Figure 2:
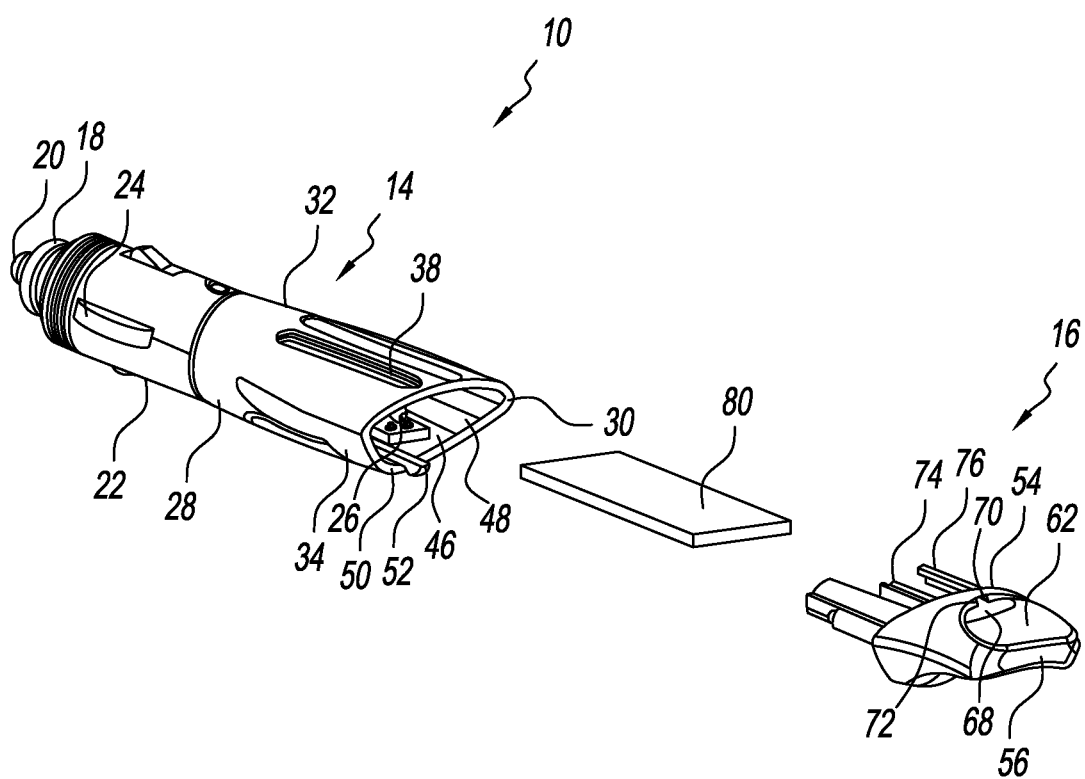
FIG. 2 is a perspective view of a scent diffuser.
Figure 3:
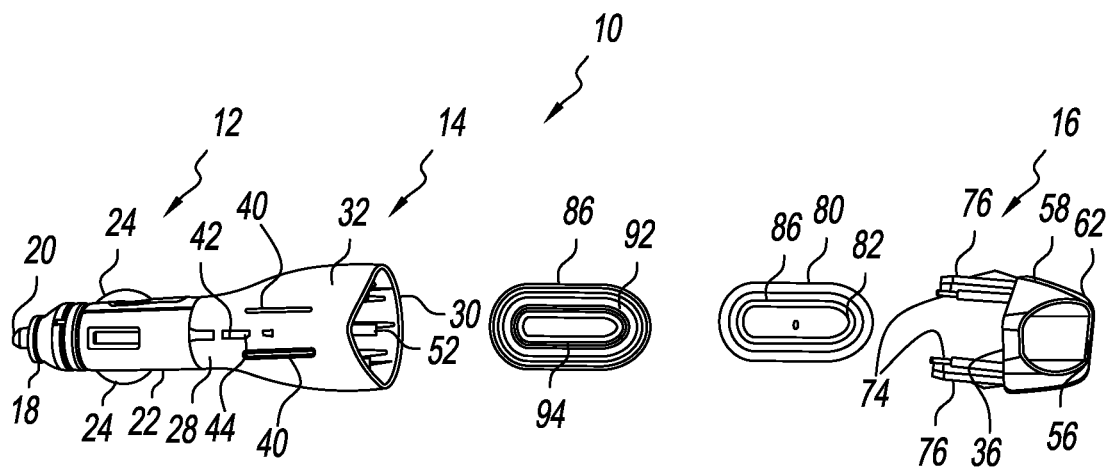
FIG. 3 is a bottom perspective view of a scent diffuser.
Figure 4:
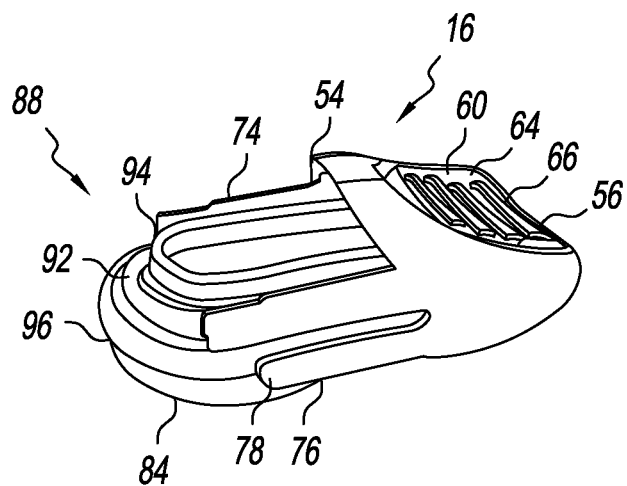
FIG. 4 is an end view of a cap.

Referring to the Figures, an ergonomic scent diffuser 10 has a first housing 12, a second housing 14, and a cap 16.

The first housing 12 is adapted to be received within a power source (not shown) such as a 12-volt socket. Extending through a first end 18 of the first housing 12 is a spring loaded positive electrode 20 and extending through a side wall 22 of the first housing 12 are a pair of negative electrodes 24. The positive 20 and negative 24 electrodes are connected to a circuit board (not shown) and are adapted to provide power to a heating member 26.

The heating member 26 is connected to a circuit board (not shown) and is disposed within the second housing 14. The circuit board is covered with a conformal coating to protect the circuit board from fragrance residue and corrosion from humidity, spills and the like. The second housing 14 is connected to the first housing 12 and has a first end 28, a second end 30, a top 32, and a bottom 34 that form a hollow chamber 36. Viewing the second housing 14 from the top, the width of the second housing 14 increases as the housing 14 extends from the first end 28 to the second end 30 to create a fin like shape. Also, viewing the second housing 14 from the ends, the second housing 14 transitions from a circular profile or shape at the first end 28 to a generally triangular profile or shape at the second end 30. The top 32 is arcuate and convex in relation to the bottom 34 and has a plurality of elongated air vents 38. The bottom 34 has a plurality of elongated air vents 40 and an elongated slot 42 through which a switch 44 extends. The switch is connected to the circuit board (not shown) and is adapted to turn the diffuser on and off as well as to set the diffuser on high or low power. The switch is also adapted to include an indicator light, illuminating when the unit is on and working. The diffuser is programmed to shut-off after a specified time period. A reset button is included. Extending inwardly toward the top 32 on an inner surface 46 of the bottom 34 are a pair of guide grooves 48 that preferably are arcuate in shape. Also, extending away from the second end 30 toward the cap 16, at a transition point 50 of the bottom 34, is a retaining clip 52.

The cap 16 is removably connected to the second end 30 of the second housing 14. The cap 16 has an open first end 54, a closed second end 56, a top 58, and a bottom 60 that form a chamber. The top 58 and bottom 60 are generally tapered as the cap 16 extends from the first end 54 toward the second end 56. Adjacent the second end 56, the top 58 has a depression 62 adapted to receive an individual's thumb. Likewise, adjacent the second end 56, the bottom 60 has a depression 64 with parallel spaced raised ridges 66 adapted to receive an individual's finger. Adjacent the first end 54 the bottom 34 has an opening 68 with a retaining slot 70 located at a transition point 72.

Extending from the second end 56 of the cap 16, through the chamber and beyond the first end 54 are a pair of guide rails 74. The guide rails 74 are positioned to align with and be slidably received within the guide grooves 48 of the second housing 14.

Also extending from the second end 56 of the cap 16 through the chamber and beyond the first end 54 are a pair of retaining members 76. The retaining members 76 dwell in a horizontal plane above the guide rails 74 and in a vertical plane outside or wider than the guide rails 74. The retaining members 76 have an elongated groove 78.

The guide rails 74 and retaining members 76 are positioned to slidably receive and retain a fragrance emitting member 80 such as a pad or the like. In a preferred example, the fragrance emitting member 80 is a rubber like fragrance block. The block 80 has a top 82, a bottom 84, and a u-shaped flange 86 that extends downwardly from the bottom 84 and away from the top 82. The block 80 is received within a block cover or tray 88 having an open top and a bottom 92 with an outwardly extending groove 94.

In operation, the block 80 is inserted into the block cover or tray 88 such that the u-shaped flange 86 of the block 80 is received within the groove 94 of the block cover or tray 88. The block cover or tray 88 is then slid into the retaining members 76. More specifically, an outer edge 96 of the block cover or tray 88 is slidably received within the elongated grooves 78 of the retaining members 76 while the groove 94 of the block cover or tray 88 slides between guide members 74.

The cap 16 is then connected to the second housing 14 by aligning the guide rails 74 with the guide grooves 48 and sliding the rails 74 along grooves 48 until retaining clip 52 snaps into slot 70 of opening 68. The diffuser 10 is then inserted into a power supply (not shown) and activated with a switch 44.

Once activated, power is supplied to the heating member 26 which provides heat that causes the fragrance block to evaporate to a scented gas that flows through air vents 38.

To replace the fragrance block 80, the cap 16 is grasped with one's thumb and finger and manual force is applied pulling the cap 16 away from the second housing 14 to overcome the engagement of the retaining clip 52 with slot 70.

Accordingly, a scent diffusing device has been disclosed that at the very least meets all the stated objectives. The design has the capacity to hold more fragrance and the cap has an ergonomic design to reduce user error.

What is claimed is:

1. An ergonomic scent diffuser, comprising:
   a first housing having a plurality of electrodes;
   a second housing connected to the first housing wherein the second housing has a heating member disposed entirely within the second housing and adapted to receive power from the plurality of electrodes; and
   a cap slidably connected to the second housing and adapted to retain a fragrance emitting member, wherein the fragrance emitting device is a block having a top, a bottom, and a U-shaped flange that extends downwardly from a bottom of the block and is configured to retain the block in a tray.

2. The diffuser of claim 1 wherein a width of the second housing increases as the second housing extends from a first end to a second end.

3. The diffuser of claim 1 wherein the second housing has grooves that extend inwardly from an inner surface of a bottom toward a top and are positioned to align with and slidably receive guide rails attached to the cap.

4. The diffuser of claim 1 wherein the second housing has a retaining clip positioned to removably connect to a slot in an opening of the cap.

5. The diffuser of claim 1 wherein the cap has a first end, a second end, a top, a bottom and a depression on both the top and the bottom adjacent the second end that are adapted to receive a thumb and a finger.

6. The diffuser of claim 1 wherein the cap has a pair of guide rails and a pair of retaining members that extend from a second end to beyond a first end.

7. The diffuser of claim 1 wherein an end profile of the second housing transitions from circular to triangular as the second housing extends from a first end to a second end.

8. The diffuser of claim 1 further comprising a tray having an outwardly extending groove, and the block received within the tray.

9. The diffuser of claim 1 further comprising a tray having an outer edge that is received within a groove of a pair of retaining members extending from the cap.

10. An ergonomic scent diffuser, comprising:
    a first housing having a plurality of electrodes;
    a second housing connected to the first housing wherein the second housing has a heating member within the second housing and adapted to receive power from the plurality of electrodes; and
    a cap slidably connected to the second housing and adapted to retain a fragrance emitting member, wherein the fragrance emitting device comprises a block and a tray having an outwardly extending groove, and the block is received within the tray.

11. The diffuser of claim 10, wherein the block is comprised of a rubber-like fragrance block.

12. The diffuser of claim 10 further comprising the block having a top, a bottom, and a U-shaped flange that extends downwardly from a bottom of the block and is configured to retain the block in a tray.

13. The diffuser of claim 10 further comprising the tray having an outer edge that is received within a groove of a pair of retaining members extending from the cap.

14. An ergonomic scent diffuser, comprising:
    a first housing having a plurality of electrodes;
    a second housing connected to the first housing wherein the second housing has a heating member within the second housing and adapted to receive power from the plurality of electrodes; and
    a cap slidably connected to the second housing and adapted to retain a fragrance emitting member;
    wherein the cap has a pair of guide rails and a pair of retaining members that extend from a second end of the cap to beyond a first end of the cap;
    wherein the retaining members dwell in a horizontal plane above the guide rails and in a vertical plane outside the guide rails.

* * * * *